US007457450B2

(12) United States Patent
Bruder et al.

(10) Patent No.: US 7,457,450 B2
(45) Date of Patent: Nov. 25, 2008

(54) METHOD FOR RECORDING AND EVALUATING IMAGE DATA WITH THE AID OF A TOMOGRAPHY MACHINE

(75) Inventors: Herbert Bruder, Hoechstadt/Aisch (DE); Thomas Flohr, Uehlfeld (DE); Bjoern Heismann, Erlangen (DE); Rainer Raupach, Adelsdorf (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 508 days.

(21) Appl. No.: 11/043,965

(22) Filed: Jan. 28, 2005

(65) Prior Publication Data

US 2005/0163283 A1 Jul. 28, 2005

(30) Foreign Application Priority Data

Jan. 28, 2004 (DE) ................... 10 2004 004 295

(51) Int. Cl.
*G06K 9/00* (2006.01)
(52) U.S. Cl. .................... 382/130; 378/4; 378/901
(58) Field of Classification Search ......... 382/128, 382/129, 130, 131, 132, 133, 134; 378/4, 378/5, 16, 19, 21–27, 98.4, 98.6, 98.9, 98.11, 378/101, 46, 63, 90, 92, 140, 901; 600/407, 600/410, 411, 425; 424/9.4; 250/363.04, 250/370.09
See application file for complete search history.

(56) References Cited

U.S. PATENT DOCUMENTS

| | | | | |
|---|---|---|---|---|
| 4,149,081 A | * | 4/1979 | Seppi | 378/5 |
| 4,247,774 A | * | 1/1981 | Brooks | 378/19 |
| 4,811,373 A | * | 3/1989 | Stein | 378/54 |
| 4,991,190 A | * | 2/1991 | Mori | 378/9 |
| 6,531,280 B1 | | 3/2003 | Pfreundschuh | |
| 6,663,988 B2 | * | 12/2003 | Shimizu et al. | 428/826 |
| 6,819,738 B2 | * | 11/2004 | Hoffman | 378/19 |
| 6,990,175 B2 | | 1/2006 | Nakashima et al. | |

(Continued)

FOREIGN PATENT DOCUMENTS

CN 1411786 A 4/2003

(Continued)

OTHER PUBLICATIONS

B.J. Heismann et al., "Density and atomic number measurements with spectral x-ray attenuation method", Journal of Applied Physics, vol. 94, No. 3, Aug. 1, 2003, pp. 2073-2079.

*Primary Examiner*—Abolfazl Tabatabai
(74) *Attorney, Agent, or Firm*—Harness, Dickey & Pierce, P.L.C.

(57) ABSTRACT

A method is for recording and evaluating image data with the aid of a tomography machine. At least two recordings with different spectral distribution are made of an examination area of an object. Further, measured data obtained from the two recordings are evaluated such that additional information relating to the examination area and/or a specific representation of the image of the examination area are/is obtained from the different spectral distributions. The tomography machine includes at least two separate recording systems. Further, it is operated such that the two recording systems operate with a different spectral distribution. As such, the additional information and the specific representation of an image can be obtained in conjunction with a reduced scanning time.

20 Claims, 4 Drawing Sheets

U.S. PATENT DOCUMENTS

| | | |
|---|---|---|
| 7,158,611 B2 | 1/2007 | Heismann et al. |
| 2003/0076927 A1 | 4/2003 | Shigeyuki |

FOREIGN PATENT DOCUMENTS

| | | |
|---|---|---|
| CN | 1136914 A | 2/2004 |
| DE | 101 43 131 A1 | 4/2003 |
| DE | 10143131 A1 | 4/2003 |
| DE | 103 02 565 A1 | 8/2004 |
| WO | WO 0324331 A2 | 3/2003 |

* cited by examiner

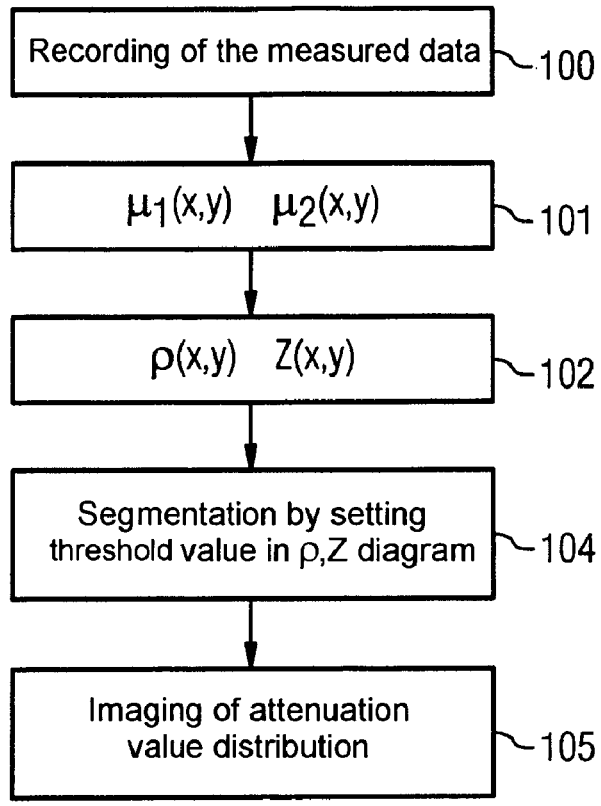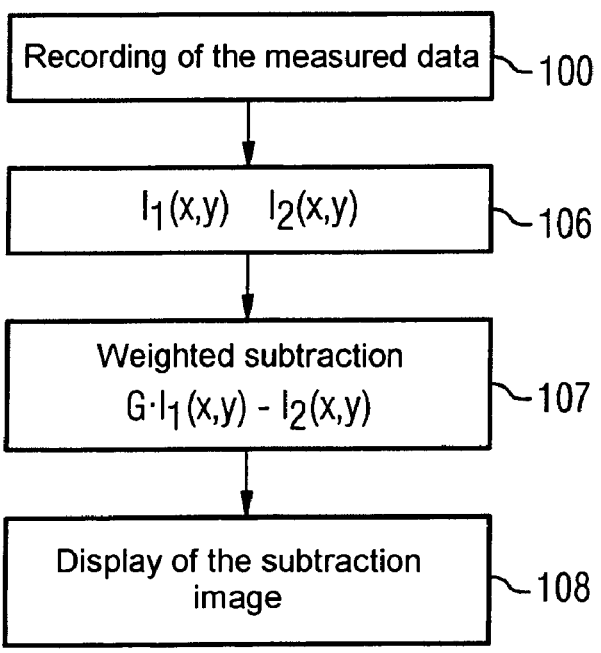

METHOD FOR RECORDING AND EVALUATING IMAGE DATA WITH THE AID OF A TOMOGRAPHY MACHINE

The present application hereby claims priority under 35 U.S.C. §119 on German patent application numbers DE 10 2004 004 295.0 filed Jan. 28, 2004, the entire contents of which is hereby incorporated herein by reference.

FIELD OF THE INVENTION

The present invention generally relates to a method for recording and evaluating image data with the aid of a tomography machine. Preferably, at least two recordings with different spectral distribution are made of an examination area of an object. Measured data obtained from the two recordings are then evaluated such that additional information relating to the examination area and/or a specific representation of the image of the examination area are/is obtained from the different spectral distributions.

BACKGROUND OF THE INVENTION

The result of radiographic methods such as, for example, computed tomography, mammography, angiography, the X-ray inspection technique or comparable methods, is firstly the representation of the attenuation of an X-ray beam along its path from the X-ray source to the X-ray detector in a projection image. This attenuation is caused by the transirradiated materials along the beam path. Thus, the attenuation can also be understood as a line integral over the attenuation coefficients of all the voxels along the beam path.

Particularly in the case of tomography methods, for example in X-ray computed tomography (CT), it is possible to employ reconstruction methods to calculate backwards from the projected attenuation data to the attenuation coefficients $\mu$ of the individual voxels, and thus to attain a substantially more sensitive examination than in the case of simply viewing projection images.

Instead of the attenuation coefficient $\mu$, in order to represent the attenuation distribution use is generally made of a value, the so-called CT number normalized to the attenuation coefficient of water. This CT number is calculated from an attenuation coefficient $\mu$, currently determined by measurement, and the reference attenuation coefficient $\mu_{H2O}$ using the following equation:

$$C = 1000 \times \frac{\mu - \mu_{H2O}}{\mu_{H2O}} [\mathrm{HU}],$$

Where the CT number C is in Hounsfield units [HU]. The result for water is a value of $C_{H2O}=0$ HU, and for air a value of $C_L=-1000$ HU. Since both representations can be transformed into one another or are equivalent, in what follows the generally selected term of attenuation value or attenuation value coefficient denotes both the attenuation coefficient $\mu$ and the CT value.

Modern tomography machines such as, for example, X-ray computed tomography machines or C arc machines are used for recording and evaluating images in order to represent the three-dimensional attenuation distribution. X-ray computed tomography machines generally have a recording system with an X-ray tube and a detector, situated opposite the latter, for detecting the radiation emanating from the X-ray tube and penetrating the object. The recording system rotates several times about the examination object during recording.

C arc machines, which are frequently used for imaging during surgical operations, include one or two so-called C arc systems as recording systems that are each moved through an angle >180° about the object to be examined during recording of the image data. The measured data supplied by the recording systems are further processed in an evaluation unit in order to obtain the desired tomogram or volumetric image of the examination area.

U.S. Pat. No. 4,991,190 A also discloses an X-ray computed tomography machine that has a number of recording systems capable of revolving about a common rotation axis. The advantage of such tomography machines having a number of recording systems by comparison with a machine with only one recording system resides in the increased data recording rate, which leads to a shorter recording time and/or increased temporal resolution. A shortened recording time is advantageous because this minimizes movement artifacts in the reconstructed image, these artifacts possibly being caused by movement of the patient or of the patient's organs such as, the heart, for example, while image data are being recorded. An increased temporal resolution is required, for example, in order to represent movement cycles when the data required for reconstructing an image need to be recorded in the shortest possible time. An imaging tomography unit having at least two recording systems is also disclosed, for example, from DE 103 03 565, which is not a prior publication.

The attenuation value distribution of such X-ray images cannot, however, be used to deduce the material composition of an examination object, since the X-ray absorption is determined both by the effective atomic number of the material and by the material density. Materials and/or tissues of different chemical and physical composition can therefore exhibit identical attenuation values in X-ray images.

In order to enhance the informativeness of an X-ray image based on the local attenuation coefficient, it is therefore known, for example from U.S. Pat. No. 4,247,774 A, to use mutually differing X-ray spectra or X-ray quantum energies to produce an X-ray image. This method used in the field of computed tomography and generally also denoted as 2-spectra CT utilizes the fact that materials of higher atomic number absorb low-energy X-radiation much more strongly than materials of lower atomic number. By contrast, in the case of higher X-ray energies the attenuation values are equal to one another and are predominantly a function of the material density. By calculating the differences in the X-ray images recorded in conjunction with different X-ray tube voltages, it is therefore possible to obtain additional information relating to the materials on which the individual image areas are based.

Yet more specific items of information are obtained when, in addition, the method of so-called base material decomposition is applied to X-ray images. In this method the X-ray attenuation values of an object to be examined are measured with the aid of X-ray beams of lower and higher energy, and the values obtained are compared with the corresponding reference values of two base materials such as, for example, calcium for skeletal material and water for soft part tissues. It is assumed here that each measured value can be represented as a linear superposition of the measured values of the two base materials. Thus, a skeletal component and a soft tissue component can be calculated for each element of the pictorial representations of the object to be examined from the comparison with the values of the base materials, thus enabling a transformation of the original pictures into representations of the two base materials.

German patent application DE 101 43 131 A1 further discloses a method whose sensitivity and informativeness further exceeds the base material decomposition and, for example, enables a functional CT imaging of high informativeness. The method can be used to calculate the spatial distribution of the density $\rho(r)$ and the effective atomic number $Z(r)$ by evaluating spectrally influenced measured data of an X-ray apparatus, also denoted as $\rho$-Z projection below. Body constituents such as, for example, iodine or the like can be determined quantitatively from a combined evaluation of the distribution of the density and effective atomic number and, for example, instances of calcification can be removed by segmentation on the basis of the atomic number.

The recording of the image data with different spectral distributions that is necessary in the case of the last-named methods is frequently implemented by operating the X-ray source of the recording system successively with different tube voltages. It is also known to use different radiation filters or energy-sensitive detectors. However, these techniques favor the disturbing influence of patient movement, require a longer scanning time and also an increased administration of contrast medium in the case of CT examinations based on contrast medium.

SUMMARY OF THE INVENTION

An object of an embodiment of the present invention is to specify a method for recording and evaluating image data with the aid of a tomography machine which permits the image data to be recorded in conjunction with different spectral distributions for the purpose of evaluating the image data in accordance with the methods. Preferably, it avoids at least one of the above disadvantages.

An object may be achieved with the aid of a method. Advantageous refinements of the method can be gathered from the following description and the exemplary embodiments.

In the case of the present method of an embodiment for recording and evaluating image data with the aid of a tomography machine, at least two recordings with different spectral distribution are made of an examination area of an object. Measured data obtained from the two recordings are evaluated such that additional information relating to the examination area and/or a specific representation of the image of the examination area are/is obtained from the different spectral distributions. The method may be distinguished in that, for the purpose of recording image data, a tomography machine having at least two separate recording systems may be used and operated such that the two recording systems operate with a different spectral distribution.

By using a tomography machine having at least two recording systems, it is possible in accordance with the method of an embodiment to acquire spectral measured data in a single scan and use them to obtain, for example, quantitative additional information relating to the examination area, in particular to the materials contained therein, by way of the 2-spectra method or the $\rho$-Z projection. The problem of patient movement may be reduced or even eliminated, since the detectors assigned to the two X-ray tubes of the two recording systems acquire the measured or attenuation data at the same time. By comparison with the conventional methods for acquiring spectral measured data, the scanning time may be halved because, for example, the required spectral volumetric data are obtained in a single spiral scan. It is also possible to use a C arc system with at least two C arcs as a tomography machine. However, it is preferred to use an X-ray computer tomography machine having at least two recording systems, also denoted below as 2 tube detector CT system.

In a further application of an embodiment of the present method, the simultaneously obtained spectral measured data are used for segmenting constituents of the examination area in the pictorial representation of imaging bone or soft part tissue, for example, in order to achieve a specific representation of the image without specific constituents. This is explained in more detail further below.

In the case of an embodiment of the present method, the two recording systems are preferably operated with different tube voltages and/or different radiation filters per tube. Also possible, however, are refinements in the case of which the two recording systems have spectrally differing selective detectors so that the different spectral distribution is achieved in the recordings by the different spectral sensitivity of the detectors.

The evaluation of the spectral measured data can be performed in the case of the present method in order to obtain the distribution of the density $\rho(r)$ and of the atomic number $Z(r)$ of the examination area as this is known from DE 101 43 131 A1 mentioned at the beginning, and whose disclosure content as regards the selection of the spectral distributions and the evaluation is explicitly incorporated into the present patent application by reference. Further fundamentals relating to such recording and evaluation of image data are to be found, for example, in B. Heismann et al., Density and Atomic Number Measurements with Spectral X-Ray Attenuation Method, J. of Appl. Phys., Vol. 94, No. 3, 2003, 2073-2079, the contents of which are also incorporated herein by reference.

It is also possible, of course, in the case of an embodiment of the present method, to evaluate in accordance with the known 2-spectra method as was likewise cited in the introductory part of the present description.

In one refinement of the method, the measured data acquired by the two recording systems are respectively used to reconstruct in a known way separate images, in particular 2D tomographs or 3D volumetric images of the attenuation value distribution. By suitable weighting of the image data of the two images and subsequent subtraction, it is then possible to eliminate from the subtraction image specific constituents of the examination object in the pictorial representation, for example, bones visible in the images.

In the example of the bones, the weighting can be selected in such a way that the bone contrast is suppressed in the subtraction image. In this case, the weighting factor is virtually independent of the actual composition of the bone, that is to say the level of the calcium fraction. The soft part contrast in the image should likewise vanish in the weighted subtraction, since the contrast difference of the soft part tissue is negligible for different voltages or different instances of prefiltering to which the recordings with the aid of the two recording systems are subjected.

It is therefore possible to use this variant of the present method primarily to carry out advantageously angiographic CT examinations where it is necessary to segment bones in order to represent blood vessels near the bone. It is likewise desirable to suppress the image signal from soft part tissue when the contrast/noise ratio in the blood vessels filled with contrast medium is relatively low.

To date, the segmentation of bones has partly required intensive post-processing of the image data. In the case of subtraction CT angiography (CTA), soft part contrasts have so far been removed with the aid of image data from an additional native scan. Here, an image of the examination area is firstly recorded without administration of contrast medium, in order subsequently to subtract this mask image from the images recorded with contrast medium. However, patient movements between the native scan and the subsequent image recordings lead in this case to a worsening of the image result. This problem no longer occurs with the present configuration of the method, since the image data of the two recordings subtracted from one another are acquired simultaneously.

A further application of the last-named subtraction method is suggested in the case of CTAs for the purpose of representing the pulmonary perfusion, in the case of which CTAs there has hitherto likewise been a need for an additional native scan to remove the soft part background. The consequence of this is that the movement of the blood vessels in the lung can substantially impair the quality of the subtraction CTA. Because the detectors assigned to the two X-ray tubes acquire the attenuation data simultaneously in the present method, the spectral data are measured simultaneously, thereby avoiding problems due to a movement of the blood vessels.

In a further refinement of the present method, in the case of which the aim is also to achieve a specific representation of the image by suppressing individual image constituents of the examination area, the first step is to use the spectral data to calculate the spatial distribution of the mean density $\rho(r)$ and of the effective atomic number $Z(r)$ in accordance with the $\rho$-Z projection already mentioned. Soft part tissue and bone can then be segmented in a $\rho,Z(r)$ diagram by setting a threshold value. It is then possible after this segmentation to represent (as attenuation value image) those voxels in the examination volume that were identified as containing iodine in the $\rho,Z(r)$ diagram. Because of the relatively high atomic number of iodine, this permits a single representation of the blood vessels filled with blood contrast medium. This method variant is therefore also suggested chiefly for angiographic CT examinations in order to avoid influences due to patient movement, or an additional native scan.

BRIEF DESCRIPTION OF THE DRAWINGS

The present invention is explained in more detail below with the aid of exemplary embodiments in conjunction with the drawings, in which:

FIG. 4 shows a second example of a flowchart for carrying out an embodiment of the present method; and FIG. 5 shows a third example of a flowchart for carrying out an embodiment of the present method.

DETAILED DESCRIPTION OF THE EXEMPLARY EMBODIMENTS

Figure 1:
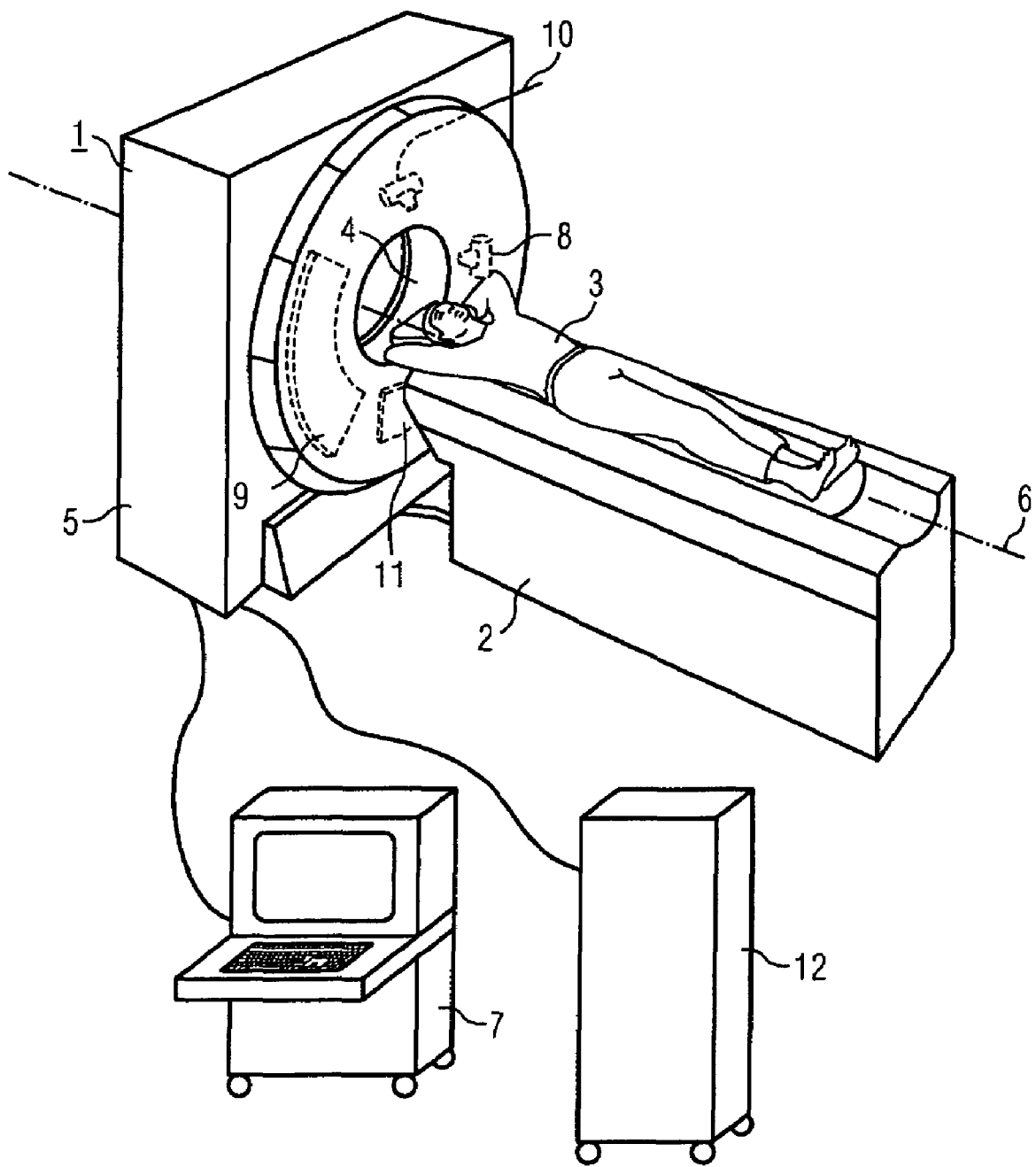
FIG. 1 shows an example of a tomography machine having two recording systems as used in an embodiment of the present method, in a perspective overall illustration.

FIG. 1 shows a tomography machine 1, in the present example an X-ray computed tomography machine, having an assigned support device 2 for receiving and supporting a patient 3. The patient 3 with the desired examination area can be introduced into an opening 4 in the housing 5 of the tomography machine 1 by way of a moveable table plate of the supporting device 2. During a spiral scan, the supporting device 2 is useful, however, to effect continuous axial feeding. A gantry (not visible in FIG. 1) can be rotated in the interior of the housing 5 at high speed about a rotation axis 6 running through the patient 3. An operating unit 7 is also present for operating the tomography machine 1.

The present tomography machine 1 has two recording systems on the gantry, and these respectively include an X-ray tube 8 or 10 respectively, and a multirow X-ray detector 9 and 11 respectively. The arrangement of the two X-ray tubes 8, 10 and the two detectors 9, 11 on the gantry is fixed during operation of the tomography machine 1, and so their relative spacings are also constant during operation.

The X-ray detectors 9, 11 are produced on the basis of an electronically readable scintillator ceramic, a so-called UFC ceramic. It is also possible to make use of so-called area detectors, for example with 256 or more rows.

In the case of the present method, the two recording systems are operated within a different spectral distribution, that is to say with a different tube voltage and/or different spectral filters in the beam path between the X-ray tube 8, 10 and the associated detector 9, 11. A different spectral sensitivity of detector 9 and detector 11 is also, of course, possible.

The projection data of the two continuously scanning recording systems are further processed in accordance with the present method in a control and imaging computer 12, and are processed to form the desired image by applying an image reconstruction algorithm. This may involve a CT image or else an illustration of a density or atomic number distribution in accordance with the following exemplary embodiments.

Figure 2:
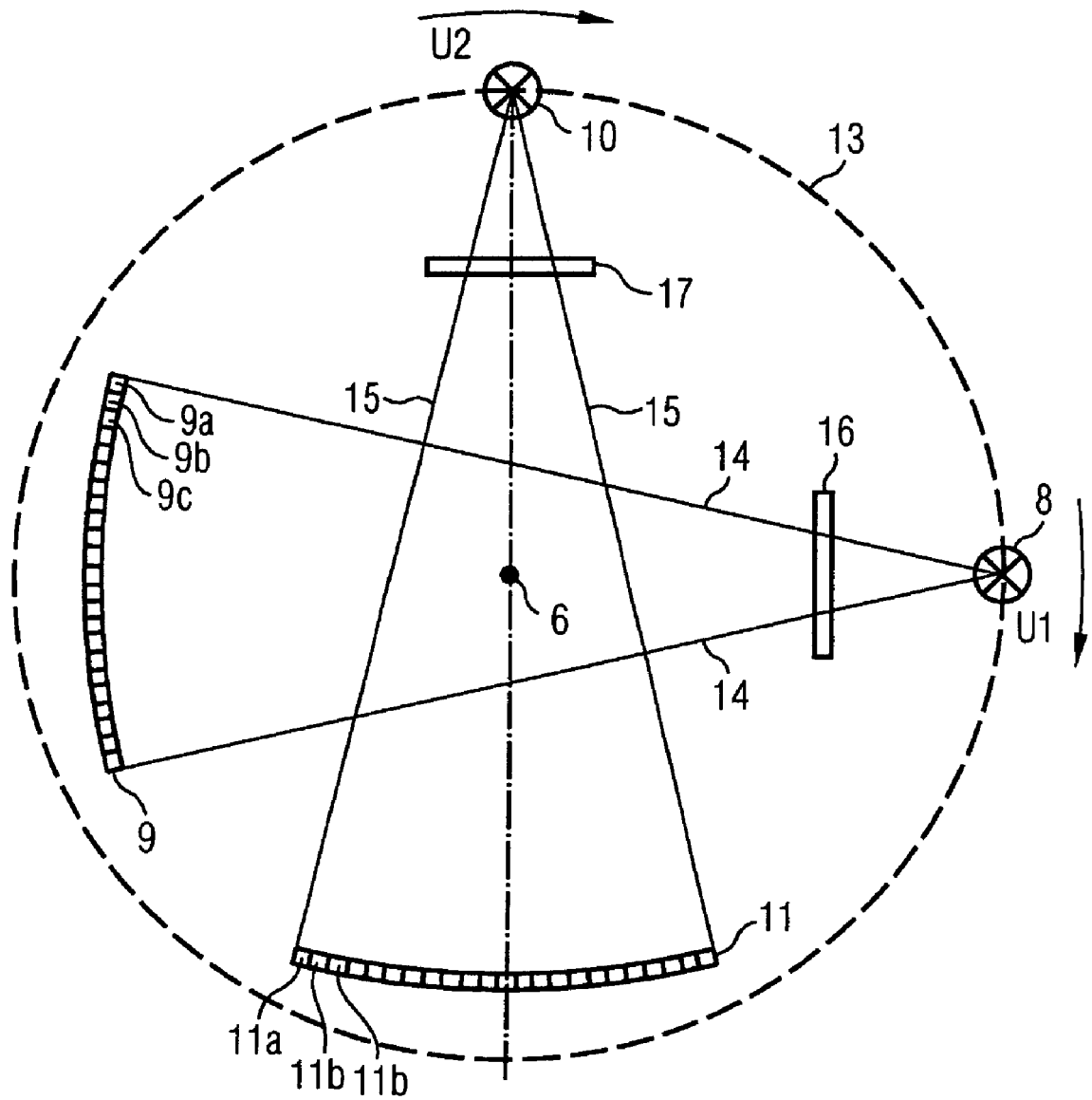
FIG. 2 shows two recording systems of the tomography machine of FIG. 1, in a cross-sectional illustration.

FIG. 2 shows the two recording systems in detail once more. It is to be seen, in particular, how the two X-ray tubes 8, 10 revolve about the rotation axis 6 in the direction of the arrow on a common circulating track 13, while raw data are generated for a subsequent image reconstruction from different projection angles. The cross-sectional illustration of FIG. 2 respectively shows a row of the detectors 9 and 11 with in each case a number of detector elements $9a, 9b, 9c, \ldots$ or $11a, 11b, 11c, \ldots$. Also to be seen from the figure are the edge rays 14 or 15 of the X-ray beams emanating from the X-ray tubes 8 or 10.

In the present example, there are introduced into the X-ray beams of the two recording systems filters 16 and 17, respectively, which in accordance with one refinement of the present method have different spectral filter characteristics. Furthermore, $U_1$ and $U_2$ indicate the different tube voltages with the aid of which the two X-ray tubes 8 and 10 can be operated.

In the case of an embodiment of the present method, such a tomography machine is operated with different tube voltages $U_1/U_2$ and/or different spectral filter characteristics of the filters 16 and 17, and so image and measured data, having the different spectral distributions are recorded simultaneously with each measuring scan. These data are further processed by the imaging computer 12 in the desired way in order to obtain additional information, for example a spatial distribution of the density or of the effective atomic number.

Figure 3:
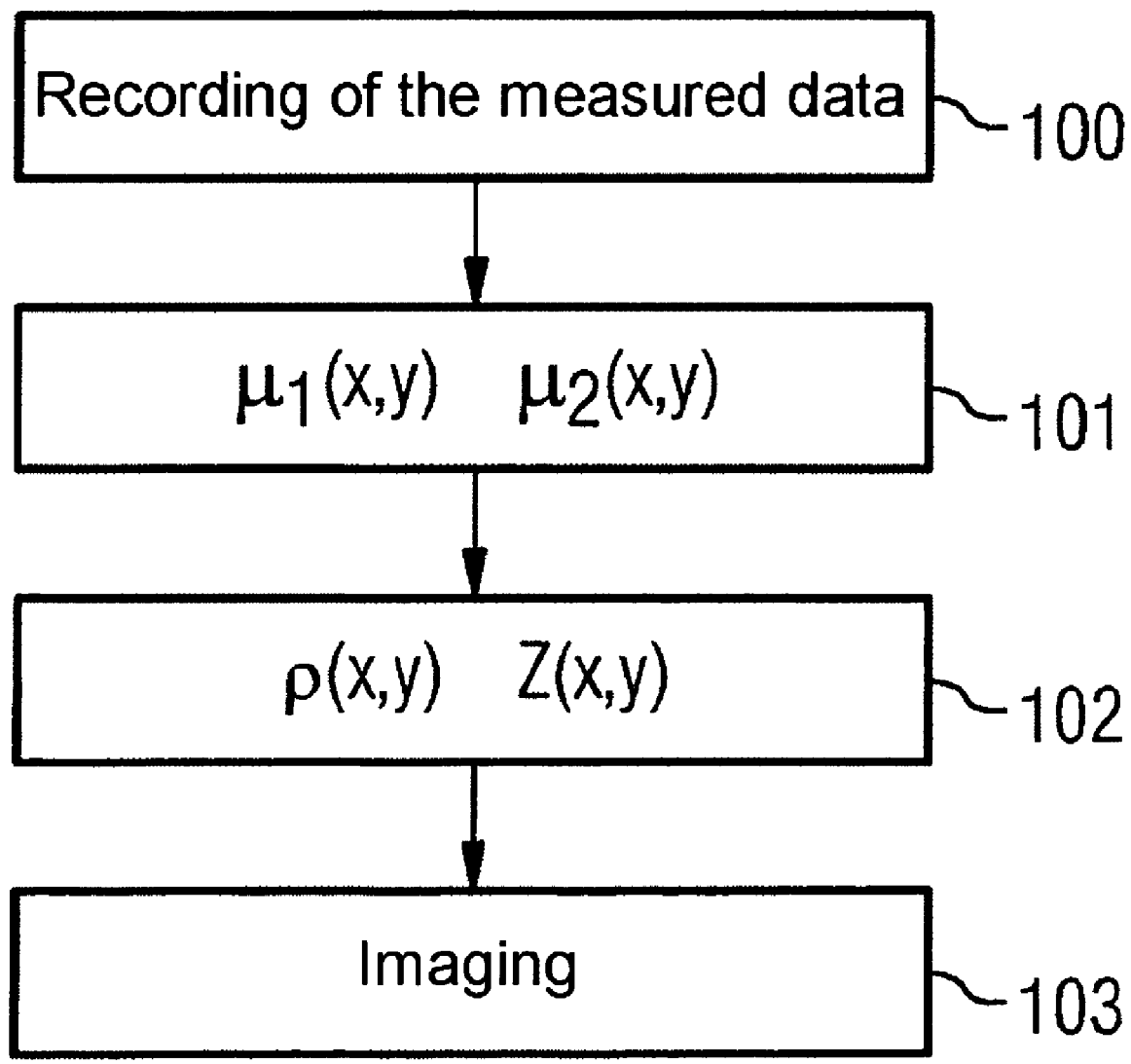
FIG. 3 shows a first example of a flowchart for carrying out an embodiment of the present method.

FIG. 3 shows an example of the cycle of an embodiment of the present method, in which the X-ray images are recorded in a first step 100 with the aid of the computer tomography machine 1 illustrated in FIGS. 1 and 2. Two separate raw data records are obtained in conjunction with a different spectral distribution by means of this recording of images of the examination area of the object to be examined.

Subsequently, in the next step 101 an attenuation value distribution $\mu_1(x,y)$ and $\mu_2(x,y)$, respectively, of the attenuation coefficient $\mu$ within a transverse tomogram with the coordinates x and y is produced via an image reconstruction based on the raw data obtained in relation to each of the spectral distributions.

In step 102, the distributions of the attenuation coefficients are transformed with the aid of a computer into an atomic number distribution Z(x,y) and a density distribution ρ(x,y). The computer-aided transformation of the attenuation value distributions into the atomic number distribution and the density distribution can be carried out, for example, using the method of DE 101 43 131 A1, to which reference is expressly made.

The distributions obtained in this way can subsequently be visualized on a monitor in a suitable way in step 103.

The selection of the different spectral distributions of the two recording systems is performed in the case of the present method such that the desired additional information and/or the desired evaluation and/or pictorial representations are/is as informative as possible. The X-ray spectrum of one recording system in this case preferably has a quantum energy that in relation to the quantum energy of the other recording system favors X-ray absorption by the photo-effect, resulting in a high resolution in the determination of the atomic numbers.

FIGS. 4 and 5 show further examples for carrying out an embodiment of the present method in the way they are advantageous in particular in the field of CT angiography. Here, before images are recorded the patient is injected with a contrast medium in order clearly to emphasize the blood streams in the CT image.

In a refinement of embodiment of the method illustrated in FIG. 4, steps 100 to 102 are carried out in the same way as for the method of FIG. 3. Soft part tissue and bone can be segmented in ρ,Z diagram in step 103 by setting a threshold value of the atomic number. The blood vessels filled with the contrast medium can thereby be displayed on the sole basis of the relatively high atomic number of the iodine-containing contrast medium. This is performed in step 105, in which only those voxels in the examination volume that are identified as containing iodine in the ρ,Z diagram on the basis of the high atomic number are displayed. The pictorial representation therefore shows a CT image of the attenuation values in which only the blood vessels filled with contrast medium are visible.

Finally, FIG. 5 shows an example where the method is carried out by reconstructing two separate images $I_{1(x,y)}$ and $I_{2(x,y)}$ from the separated raw data of the two recording systems in step 106 after recording image data in step 100. In the next step 107, image data of one of the two images $I_{1(x,y)}$ multiplied by a weighting factor G selected in such a way that the bone fractions in the subtraction image are no longer to be seen after subtraction of the weighted image data from the unweighted one (or vice versa). This subtraction image is subsequently displayed on a monitor in step 108.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for creating recordings and evaluating data with the aid of a tomography machine, comprising:
    creating at least two recordings, with different spectral distribution, of an examination area of an object; and
    evaluating measured data obtained from the two recordings such that additional information relating to at least one of the examination area and a specific representation of the image of the examination area is obtained from the different spectral distributions,
    wherein the tomography machine includes at least two separate recording systems, each of the at least two recording systems including a separate X-ray tube and a separate detector, and
    wherein the two recording systems operate with different spectral distributions.

2. The method as claimed in claim 1, wherein the two recording systems are operated with a different tube voltage.

3. The method as claimed in claim 2, wherein the different spectral distribution of the two recording systems is set by different spectral filtering.

4. The method as claimed in claim 2, wherein detectors with a different spectral sensitivity are used in the two recording systems.

5. The method as claimed in claim 2, wherein the measured data of the two recordings are evaluated such that at least one of a spatial density and atomic number distribution of the examination area is obtained.

6. The method as claimed in claim 1, wherein the different spectral distribution of the two recording systems is set by different spectral filtering.

7. The method as claimed in claim 6, wherein detectors with a different spectral sensitivity are used in the two recording systems.

8. The method as claimed in claim 6, wherein the measured data of the two recordings are evaluated such that at least one of a spatial density and atomic number distribution of the examination area is obtained.

9. The method as claimed in claim 1, wherein detectors with a different spectral sensitivity are used in the two recording systems.

10. The method as claimed in claim 9, wherein the measured data of the two recordings are evaluated such that at least one of a spatial density and atomic number distribution of the examination area is obtained.

11. The method as claimed in claim 1, wherein the measured data of the two recordings are evaluated such that at least one of a spatial density and atomic number distribution of the examination area is obtained.

12. The method as claimed in claim 11, wherein a threshold value method is applied to at least one of the density and atomic number distribution in order to segment at least one of bone and soft tissue.

13. The method as claimed in claim 1, wherein the measured data of the two recordings are firstly evaluated independently of one another in order to reconstruct a first and a second attenuation value image of the examination area, and image data of the first attenuation value image are subsequently subtracted in a weighted fashion from the image data of the second attenuation value image in order to suppress specific image components in a subtraction image obtained by the subtraction.

14. The method as claimed in claim 1, wherein the measured data of the two recordings are firstly evaluated independently of one another in order to reconstruct a first and a second attenuation value image of the examination area, and image data of the first attenuation value image are subsequently subtracted in a weighted fashion from the image data of the second attenuation value image in order to suppress bone images in a subtraction image obtained by the subtraction.

15. A method for recording image data using a tomography machine including at least two separate recording systems operating with different spectral distributions, comprising:
    recording at least two images, with at least two different spectral distributions, of an examination area of an object, each of the at least two image recordings using a separate X-ray tube and a separate detector; and
    obtaining additional information relating to at least one of the examination area and a specific representation of the image of the examination area from the at least two different spectral distributions.

16. The method as claimed in claim 15, wherein the two recording systems are operated with a different tube voltage.

17. The method as claimed in claim 15, wherein the different spectral distribution of the two recording systems is set by different spectral filtering.

18. The method as claimed in claim 15, wherein detectors with a different spectral sensitivity are used in the two recording systems.

19. The method as claimed in claim 15, wherein the measured data of the two recordings are evaluated such that at least one of a spatial density and atomic number distribution of the examination area is obtained.

20. The method as claimed in claim 19, wherein a threshold value method is applied to at least one of the density and atomic number distribution in order to segment at least one of bone and soft tissue.

* * * * *